United States Patent
Shchepinov

(12) 
(10) Patent No.: US 6,734,025 B2
(45) Date of Patent: May 11, 2004

(54) METHOD FOR CALIBRATING MASS SPECTROMETERS WITH TRITYL MASS-TAGS

(75) Inventor: Mikhail Sergeevich Shchepinov, San Diego, CA (US)

(73) Assignee: ISIS Innovation, Ltd. (GB)

( * ) Notice: Subject to any disclaimer, the term of this patent is extended or adjusted under 35 U.S.C. 154(b) by 185 days.

(21) Appl. No.: 09/928,639

(22) Filed: Aug. 13, 2001

(65) Prior Publication Data

US 2002/0045269 A1 Apr. 18, 2002

Related U.S. Application Data

(60) Provisional application No. 60/248,027, filed on Nov. 13, 2000.

(30) Foreign Application Priority Data

Aug. 14, 2000 (GB) .............................................. 0019994

(51) Int. Cl.[7] .............................................. G01H 24/00
(52) U.S. Cl. ...................................... 436/173; 326/140
(58) Field of Search .................................. 436/173, 140

(56) References Cited

FOREIGN PATENT DOCUMENTS

| WO | WO 98/26095 A2 | 6/1998 |
|---|---|---|
| WO | WO 99/60007 A2 | 11/1999 |

OTHER PUBLICATIONS

Shchepinov et al. "Trityl tags for encoding in combinatorial oligonucleotide synthesis", International Symposium, 6th, York, United Kingdom, Aug. 31–Sep. 4, (2001), Meeting Date 1999, 207–212.*

Berlin et al. "Mass spectrometry of five classes of trityl compounds —loss of 12C from (C6H5)313CH [triphenylmethane–13c]", Organic Mass Spectrometry (1969), 2(5), 447–66, Abstract.*

Shchepinov, Mikhail S. et al., "Trityl Tags for Encoding in Combinatorial synthesis" *Tetrahedron* (2000), pp. 2713–2724, vol. 56.

* cited by examiner

*Primary Examiner*—Yelena G. Gakh
(74) *Attorney, Agent, or Firm*—Saliwanchik, Lloyd & Saliwanchik

(57) ABSTRACT

The subject invention relates to processes of measuring molecular mass by mass spectrometry, in particular to methods of precise calibration of mass spectrometers, and to kits and systems for use in calibrating mass spectrometers.

20 Claims, No Drawings

METHOD FOR CALIBRATING MASS SPECTROMETERS WITH TRITYL MASS-TAGS

CROSS REFERENCE TO A RELATED APPLICATION

This application claims priority to provisional patent application U.S. S No. 60/248,027, filed Nov. 13, 2000.

This invention relates to processes of measuring molecular mass by mass spectrometry, in particular to methods of precise calibration of mass spectrometers, and to kits and systems for use in calibrating mass spectrometers.

In recent years the required precision for measurements obtained by mass spectrometry has increased greatly. It is now routine that mass spectrometric data should have error not more than 1 to 5 ppm. Thus it has become increasingly important to obtain accurate calibration of mass spectrometers.

It is known to calibrate mass spectrometers by including calibration compounds of known molecular mass in the sample to be analysed. An ideal set of calibration compounds would include at least two compounds of different molecular mass, one above, one below and both close to the expected molecular mass of the material whose exact mass is to be measured. It is important that compounds of known mass have mass close to the mass to be measured, since the calibration curve is not linear.

Various types of compound are known for use as calibration compounds. These include certain sugar derivatives which can be provided with a range of molecular masses. However, they are difficult to synthesise and tend to break down during the mass spectrometry process into by-products which result in significant background noise in the spectrum. They tend also not to be particularly good flyers in the mass spectrometer.

Alternative systems are based on peptides. However these are again expensive to make. Additionally they tend to have different signal intensities and can be difficult to find in the final spectrum.

It would be desirable to provide methods and systems for calibration of mass spectrometers which include calibration compounds of accurate and predetermined molecular mass, which fly well in the mass spectrometer and which do not give rise to breakdown products which produce background noise in the spectrum. It would also be desirable to provide calibration compounds which are straightforward and inexpensive to make.

According to the invention we provide a method of measuring the molecular mass of a compound Y of unknown molecular mass by mass spectrometry, comprising providing a sample of compound Y, providing samples of at least two different compounds each of formula (I), R-X in which R is a trityl group and X is cleavable to form a charged species for mass spectrometry, and recording the molecular mass of compound Y and the at least two compounds of formula (I) in a mass spectrometer.

Thus in the invention we use the trityl compounds of formula (I) as calibration compounds in mass spectrometry. We find that the trityl groups are particularly suitable for use as calibration compounds. The trityl groups are readily cleaved from the compound of formula (I) by illumination with a laser in the mass spectrometer. Further, the resulting positively charged carbonium ion is very stable and thus sensitivity of detection is high. They also fly well in the mass spectrometer. Furthermore, the unique structure of the trityl group presents scope for a wide range of predetermined molecular masses which can be selected an controlled as appropriate depending upon the estimated molecular mass of the compound to be measured. Generally in the process the compound Y is not also of the formula R-X.

The calibration compounds are of formula R-X in which R is a trityl group. Generally R is $R^1R^2R^3C$— wherein $R^1$, $R^2$ and $R^3$ are the same or different and each is a monocyclic or fused ring aromatic group that is substituted or unsubstituted. Preferably each of $R^1$, $R^2$ and $R^3$ is aryl, preferably phenyl.

Preferably at least one of $R^1$, $R^2$ and $R^3$ carries a substituent selected from $C_1$–$C_{20}$ alkoxy or hydrocarbyl, substituted or unsubstituted. Substituents may be present at any point in the aromatic ring, but parka substituents are convenient and preferred.

When the alkoxy or hydrocarbyl is substituted the substituent is preferably selected from the group consisting of carboxylic acid, sulphonic acid, nitro, cyano, hydroxyl, thiol, primary, secondary or tertiary amino, primary or secondary amido, anhydride, carbonyl halide and active ester. In these substituents, hydrogen atoms may be partly or wholly replaced by deuterium or halogen, e.g., fluorine. This improves the range of molecular weights available. For instance, alteration of the molecular mass may be obtained by the use of non-radioactive isotopic substituents, e.g., small alkyl groups containing 1, 2 or 3 deuterium atoms.

It is preferred that the trityl group R is substituted with amide substituents. Substituted trityl groups of this type are particularly easy to produce, with a wide range of molecular masses. Thus preferably the trityl group R includes two or four or more amide substituents. More preferably $R^1$, $R^2$ and $R^3$ together carry at least two amide groups and/or at least two reactive groups for coupling, preferably N-hydroxy hydroxysuccinimide ester groups.

The group X is cleavable to form a charged species for mass spectrometry. Usually it is photocleavable, e.g., by laser illumination. X may be any suitable leaving group, for instance halide or tosylate.

In the method at least two different compounds of formula (I), having different molecular mass, are used. Preferably the number of compounds of formula (I) is larger, for instance at least 5, preferably at least 10 and even at least 20 may be desirable. The compounds of formula (I) are generally selected to have a range of molecular masses around the estimated molecular weight of compound Y. Desirably the molecular masses of the compounds of formula (I) are close to that of compound Y, for more accurate calibration. Thus in a preferred method according to the invention the molecular mass of unknown compound Y is estimated as $M_y$ and at least one compound of formula (I) having known molecular mass $M_1$ below $M_y$ is provided, as is at least one different compound of formula (I) having molecular mass $M_2$ above $M_y$. Preferably each of $M_1$ and $M_2$ lies in a molecular mass range not more than ±50% of $M_y$. That is $M_1$ is not less than 50% of $M_y$ and $M_2$ is not greater than 150% of $M_y$. Preferably the range is within ±25%, more preferably ±10%.

It is possible to provide prepared mixtures of at least two compounds of formula (I) which can be combined with a sample Y of unknown molecular mass and used as calibration compounds in mass spectrometry. Such mixtures preferably comprise at least 5, more preferably at least 10 and in some cases at least 20 different compounds of formula (I).

Thus in a second aspect of the invention we provide a method of measuring the molecular mass of a compound Y of unknown molecular mass comprising estimating the expected molecular mass of compound Y, selecting at least one calibration compound of formula (I) R-X having molecular mass close to the expected molecular mass of the compound Y, in which R is a trityl group and X is cleavable to form a charged species for mass spectrometry, and subjecting both compounds to mass spectrometry simultaneously.

In this aspect the compound of formula (I) may have any of the preferred features indicated for the first aspect of the invention above, as appropriate.

According to a third aspect of the invention we provide mixtures suitable for use in mass spectrometry as calibration compounds. According to this aspect we provide a set of calibration compounds for mass spectrometry comprising at least two separately packaged mixtures (a) and (b), wherein mixture (a) comprises at least two different compounds each of formula (I) R-X and having different molecular masses mixture (b) comprises at least two further compounds of formula (I) R-X having different molecular masses and wherein R is a trityl group and X is cleavable to form a charged species for mass spectrometry.

Thus the set comprises at least two different sets of calibration compounds. Preferably each set has molecular masses extending across a different range. The ranges may overlap. Thus preferably the lowest molecular mass in mixture (a) is lower than the lowest molecular mass in mixture (b) and the highest molecular mass in mixture (a) is lower than the highest molecular mass in mixture (b).

More preferably, the set comprises at least three separately packaged mixtures of compounds, more preferably at least five separately packaged mixtures of compounds. The greater the number of separate mixtures, the greater the scope for calibration of unknown compounds of a range of molecular masses.

Each set preferably contains at least five compounds of different molecular masses, more preferably at least ten different compounds of different molecular masses. In some cases at least twenty different compounds are desirable.

An advantage of the use of the trityl calibration compounds of the invention is that they may easily be produced to have almost any predetermined molecular weight. In particular, the trityl compounds may be produced by reacting a base reactant of formula (I) R-X with an amine. This produces an amide-substituted trityl compound. The reaction conditions may be chosen by those skilled in the art. Our earlier publication WO99/60007 describes suitable reaction conditions. In that publication we describe the use of trityl compounds as tag moieties for molecules such as oligonucleotides or oligopeptides. The techniques described there for modifying molecular mass of the trityl groups may be applied in the present invention.

According to a fourth aspect of the invention we provide a kit for the production of calibration compounds for mass spectrometry comprising:

(a) at least one base reactant of formula (I) R-X where R is a trityl group and X is cleavable to form a charged species for mass spectrometry and (b) at least two different amine compounds which are of different molecular masses and which are each capable of reacting with the base reactant and base reactant (a) is packaged separately from amine compounds (b).

This kit can be supplied to end users for reaction of base reactant (a) with amine compounds (b) as desired to create a group of compounds of formula (I) of different molecular masses. As in the earlier aspects of the invention, preferably the kit comprises at least 5, more preferably at least 10 and in some cases at least 20 different amine compounds which are of different molecular masses. Other preferred features discussed above may be applied as appropriate.

The kit can be supplied with instructions such that the end user selects at least two desired molecular masses $M_1$ and $M_2$ for the calibration compounds and chooses one or more amines for reaction with the base reactant so as to obtain compounds of formula (I) having the desired predetermined molecular masses $M_1$ and $M_2$. These compounds may then be used in mass spectrometry.

In a fifth aspect of the invention we provide a further kit for the production of a set of calibration compounds comprising a first package comprising a base reactant of formula (I) R-X, in which R is a trityl group and X is cleavable to form a charged species for mass spectrometry, and at least two separate second packages (a) and (b), each containing a mixture of at least two amine compounds which have different molecular masses and which are capable of reacting with the base reactant.

Thus the kit is suitable for producing a set of calibration compounds according to the third aspect of the invention. As in that aspect, preferably the lowest molecular mass in mixture (a) is lower than the lowest molecular mass in mixture (b) and the highest molecular mass in mixture (a) is lower than the highest molecular mass in mixture (b). The kit may contain at least three, preferably at least five mixtures, so as to provide a greater number of mixtures. Preferably each mixture contains at least five different amine compounds, more preferably at least ten different amine compounds and in some cases at least twenty different amine compounds. The invention also provides a mixture of at least two compounds of formula (I) R-X in which R is a trityl group and X is a group cleavable to give a charged species for analysis by mass spectrometry.

Preferably it comprises at least five, preferably at least ten different compounds of formula (I). The invention also provides a method of mass spectrometry comprising subjecting simultaneously to mass spectrometry at least two different compounds of formula (I) R-X in which R is a trityl group and X is cleavable to give a charged species for analysis by mass spectrometry.

Preferred features of all aspects of the invention are:

R is $R^1R^2R^3$ C— wherein $R^1$, $R^2$ and $R^3$ are the same or different and each is a monocyclic or fused ring aromatic group that is substituted or unsubstituted. At least one of $R^1$, $R^2$ and $R^3$ carries a substituent selected from $C_1$–$C_{20}$ alkoxy or hydrocarbyl, substituted or unsubstituted. The alkoxy or hydrocarbyl is substituted by carboxylic acid, sulphonic acid, nitro, cyano, hydroxyl, thiol, primary, secondary or tertiary amino, primary or secondary amido, anhydride, carbonyl halide or active ester. Each of $R^1$, $R^2$ and $R^3$ is aryl, preferably phenyl. The trityl group R includes two or four or more amide substituents. $R^1$, $R^4$ and $R^3$ together carry at least two amide groups and/or at least two reactive groups for coupling, preferably N-hydroxysuccinimide ester groups is halide or tosylate. The method comprises providing at least five, preferably at least ten compounds of formula (I) and recording their molecular masses in a mass spectrometer. The group X is photo-cleavable to form a charged species for mass spectrometry. The method additionally comprises estimating the molecular mass of unknown compound Y as $M_y$ and providing at least one compound of formula (I) which has known molecular mass $M_1$ below $M_y$ and at least one different compound of formula (I) which has molecular mass $M_2$ above $M_y$, and preferably the difference between $M_y$ and each of $M_1$ and $M_2$ is not more than ±50%. The method additionally comprises providing a sample of at least one further compound Z of unknown molecular mass and measuring the molecular mass of compound Z.

Use of a compound of formula (I) R-X in which R is a trityl group and X is cleavable to form a charged species for mass spectrometry as a calibration compound for mass spectrometry.

A kit for the production of calibration compounds for mass spectrometry comprising:
  (a) at least one base reactant of formula (I) R-X where R is a trityl group and X is cleavable to form a charged species for mass spectrometry and
  (b) at least two different amine compounds which are of different molecular masses and which are each capable of reacting with the base reactant
  and base reactant (a) is packaged separately from amine compounds (b).

A kit additionally comprising instructions to select at least two desired molecular masses $M_1$ and $M_2$ for the calibration compounds and to choose one or more amines for reaction with the base reactant so as to obtain compounds of the desired predetermined molecular masses $M_1$ and $M_2$, and instructions to use the compounds in mass spectrometry.

A set of calibration compounds for mass spectrometry comprising at least two separately packaged mixtures (a) and (b), wherein
  mixture (a) comprises at least two different compounds each of formula (I) R-X and having different molecular masses
  mixture (b) comprises at least two further compounds of formula (I) R-X having different molecular masses and wherein R is a trityl group and X is cleavable to form a charged species for mass spectrometry.

A set in which the lowest molecular mass in mixture (a) is lower than the lowest molecular mass in mixture (b) and the highest molecular mass in mixture (a) is lower than the highest molecular mass in mixture (b).

A set in which each of mixtures (a) and (b) contains at least five different compounds of different molecular masses, preferably at least 10 different compounds of different molecular masses.

A set comprising at least three separately packaged mixtures of compounds, preferably at least five separately packaged mixtures of compounds.

A kit for the production of a set of calibration compounds comprising a first package comprising a base reactant of formula (I) R-X, in which R is a trityl group and X is cleavable to form a charged species for mass spectrometry, and at least two separate second packages (a) and (b), each containing a mixture of at least two amine compounds which have different molecular masses and which are capable of reacting with the base reactant.

A kit in which the lowest molecular mass mixture (a) is lower than the lowest molecular mass in mixture (b) and the highest molecular mass in mixture (a) is lower than the highest molecular mass in mixture (b).

A kit in which each of mixtures (a) and (b) contain at least five different amine compounds of different molecular masses, preferably am least ten different amine compounds of different molecular masses.

A kit comprising at least three mixtures of amine compounds, preferably at least five mixtures of amine compounds.

A method of measuring the molecular mass of a compound Y of unknown molecular mass comprising
  estimating the expected molecular mass of compound Y,
  selecting at least one calibration compound of formula (I) R-X having molecular weight close to the expected molecular weight of the compound Y, in which R is a trityl group and X is cleavable to form a charged species for mass spectrometry
  and subjecting both compounds to mass spectrometry simultaneously.

A method in which the calibration compound R-X is provided by selecting a base reactant R-X in which R is a trityl group different from R and selecting an amine reactant of appropriate molecular mass and reacting the amine reactant and the base reactant.

The invention will now be illustrated with reference to the following example.

EXAMPLE

In this example the exact mass of a compound of formula $C_{25}H_{20}NO_5$ is determined. The calculated exact mass is 414.13415. Tr(NHS) is produced as described by Shchepinov et al in Tetrahedron 56 (2000) 2713–2724. This compound is treated with butylamine and amylamine as described in that publication. This gives two calibration compounds with exact calculated masses of 402.50781 and 416.52096. The two calibration compounds and analyte are subjected to mass spectrometry and the monoisotopic mass of the analyte was determined to be 414.13621, with an error of 4.9 ppm.

I claim:

1. A method of measuring the molecular mass of a compound Y of unknown molecular mass by mass spectrometry, comprising
    providing a sample of compound Y,
    providing a sample of at least two different compounds each of Formula (I), R-X which are calibration compounds of predetermined molecular mass, in which R is a trityl group and X is cleavable to form a charged species for mass spectrometry,
    and recording the molecular mass of compound Y and the at least two compounds of Formula (I) in a mass spectrometer,
    and comparing the recorded or measured molecular mass of compound Y to that of the at least two calibration compounds of Formula (I), correcting for any difference between the predetermined mass of the calibration compounds and their recorded mass.

2. The method, according to claim 1, in which R is $R^1R^2R^3$ C- wherein $R^1$, $R^2$ and $R^3$ are the same or different and each is a monocyclic or fused ring aromatic group that is substituted or unsubstituted.

3. The method, according to claim 2, in which at least one of $R^1$, $R^2$ and $R^3$ carries a substituent selected from the group consisting of substituted or unsubstituted $C_2$–$C_{20}$ alkoxy and hydrocarbyl.

4. The method, according to claim 3, in which the alkoxy or hydrocarbyl is substituted by a substituent selected from the group consisting of carboxylic acid, sulphonic acid, nitro, cyano, hydroxyl, thiol, primary, secondary or tertiary amino, primary or secondary amido, anhydride, carbonyl halide and active ester.

5. The method, according claim 2, in which $R^1$, $R^2$ and $R^3$ together carry at least two amide groups and/or at least two reactive groups for coupling.

6. The method, according to claim 5, wherein said groups are N-hydroxy succinimide ester groups.

7. The method, according to any of claim 2, in which each of $R^1$, $R^2$ and $R^3$ is aryl.

8. The method, according to claim 7, wherein said aryl is phenyl.

9. The method, according to claim 1, in which the trityl group R has at least two amide substituents.

10. The method, according to claim 9, wherein said trityl group R has at least four amide substituents.

11. The method, according to claim 1, in which X is halide or tosylate.

12. The method, according to claim 1, comprising providing at least five compounds of Formula (I) and recording their molecular masses in a mass spectrometer.

13. The method, according claim 1, in which the group X is photocleavable to form a charged species for mass spectrometry.

14. The method, according to claim 1, additionally comprising estimating the molecular mass of unknown compound Y as $M_y$ and providing at least one compound of Formula (I) which has known molecular mass $M_1$ below $M_y$ and at least one different compound of Formula (I) which has molecular mass $M_2$ above $M_y$.

15. The method, according to claim 14, wherein the difference between $M_y$ and each of $M_1$ and $M_2$ is not more than ±50%.

16. The method, according to claim 1, additionally comprising providing a sample of at least one further compound Z of unknown molecular mass and measuring the molecular mass of compound Z.

17. A method of using a compound of Formula (I) R-X, in which R is a trityl group and X is cleavable to form a charged species for mass spectrometry, as a calibration compound for mass spectrometry, comprising the slops of introducing the compound into a mass spectrometer, forming the charged species by cleavage of X, measuring the mass of the charged species and calibrating the mass spectrometer based on a comparison between the measured mass of the charged species and the predetermined mass of the charged species.

18. A method of measuring the molecular mass of a compound Y or unknown molecular mass comprising estimating the expected molecular mass of compound Y, selecting at least one calibration compound of Formula (I) R-X having a predetermined molecular weight close to the expected molecular weight of the compound Y, in which R is a trityl group an X is cleavable to form a charged species for mass spectrometer;

A method of measuring the molecular mass of a compound Y of unknown molecular mass comprising estimating the expected molecular mass of compound Y, selecting at least one calibration compound of Formula (I) R-X having a predetermined molecular weight close to the expected molecular weight of the compound Y, in which R is a trityl group and X is cleavable to form a charged species for mass spectrometry;

and subjecting both compounds to mass spectrometry cimultaneously to obtain the measured molecular weight of compound Y and the at least one calibration compound of Formula (I); and comparing the measured molecular weight of compound Y to that of the at least one calibration compound of Formula (I), correcting for any difference between the predetermined molecular weight and the measured molecular weight of the at least one calibration compound Formula (I).

19. The method, according to claim 18, in which the calibration compound R-X is provided by selecting a base reactant R-X and selecting an amine reactant of appropriate molecular mass and reacting the amine reactant and the base reactant.

20. A method of calibrating a mass spectrometer comprising subjecting simultaneously to mass spectrometry at least two different compounds of Formula (I) R-X, which are calibration compounds of different predetermined molecular masses, in which R is a trityl group and X is cleavable to give a charged species for analysis by mass spectrometry, thereby obtaining measured molecular masses; and calibrating the mass spectrometer based on the difference between the measured molecular masses of the calibration compounds and the predetermined molecular masses.

* * * * *

UNITED STATES PATENT AND TRADEMARK OFFICE
CERTIFICATE OF CORRECTION

PATENT NO. : 6,734,025 B2
DATED : May 11, 2004
INVENTOR(S) : Mikhail Sergeevich Shchepinov and Edwin Mellor Southern It is certified that error appears in the above-identified patent and that said Letters Patent is hereby corrected as shown below:

Title page,
Item [75] "Inventor: Mikhail Sergeevich Shchepinov, San Diego, CA (US)" should read -- Inventors: Mikhail Sergeevich Shchepinov, San Diego, CA (RU); Edwin Mellor Southern, Oxford, (GB)" --

Column 6,
Line 41, "and recording" should read -- recording --.
Line 55, "unsubstituted $C_2$-$C_{20}$" should read -- unsubstituted $C_1$-$C_{20}$ --.

Column 7,
Line 33, "the slops of" should read -- the steps of --.

Column 7, line 40 through Column 8, line 23
"18. A method of measuring the molecular mass of a compound Y or unknown molecular mass comprising
estimating the expected molecular mass of compound Y, selecting at least one calibration compound of Formula (I) R-X having a predetermined molecular weight close to the expected molecular weight of the compound Y, in which R is a trityl group an X is cleavable to form a charged species for mass spectrometer;
A method of measuring the molecular mass of a compound Y of unknown molecular mass comprising
estimating the expected molecular mass of compound Y, selecting at least one calibration compound of Formula (I) R-X having a predetermined molecular weight close to the expected molecular weight of the compound Y, in which R is a trityl group and X is cleavable to form a charged species for mass spectrometry;
and subjecting both compounds to mass spectrometry cimultaneously to obtain the measured molecular weight of compound Y and the at least one calibration compound of Formula (I); and comparing the measured molecular weight of compound Y to that of the at least one calibration compound of Formula (I), correcting for any difference between the predetermined molecular weight and the measured molecular weight of the at least one calibration compound Formula (I)" should read:
-- 18. A method of measuring the molecular mass of a compound Y of unknown molecular mass comprising
estimating the expected molecular mass of compound Y, selecting at least one calibration compound of Formula (I) R-X having a predetermined molecular weight close to the expected molecular weight of the compound Y, in which R is a trityl group and X is cleavable to form a charged species for mass spectrometry;

UNITED STATES PATENT AND TRADEMARK OFFICE
CERTIFICATE OF CORRECTION

PATENT NO.   : 6,734,025 B2
DATED        : May 11, 2004
INVENTOR(S)  : Mikhail Sergeevich Shchepinov and Edwin Mellor Southern It is certified that error appears in the above-identified patent and that said Letters Patent is hereby corrected as shown below:

<u>Column 7, line 40 through Column 8, line 23 (cont'd),</u>
subjecting both compounds to mass spectrometry simultaneously to obtain the measured molecular weight of compound Y and the at least one calibration compound of Formula (I); and comparing the measured molecular weight of compound Y to that of the at least one calibration compound of Formula (I), correcting for any difference between the predetermined molecular weight and the measured molecular weight of the at least one calibration compound Formula (I). --

Signed and Sealed this

Seventh Day of December, 2004

JON W. DUDAS
*Director of the United States Patent and Trademark Office*